United States Patent
Xian et al.

(10) Patent No.: US 11,692,186 B2
(45) Date of Patent: Jul. 4, 2023

(54) **SNAKE VENOM THROMBIN-LIKE ENZYME MARKER PEPTIDE OF *AGKISTRODON HALYS PALLAS* AND ITS APPLICATION IN THE SPECIES IDENTIFICATION OF HEMOCOAGULASE FOR INJECTION**

(71) Applicants: Shandong University, Shandong (CN); Shandong Institute for Food and Drug Control, Shandong (CN); Avanc Pharmaceutical Co., Ltd, Liaoning (CN)

(72) Inventors: Ruiqing Xian, Shandong (CN); Feng Shi, Shandong (CN); Liping Gong, Shandong (CN); Lianli Chi, Shandong (CN); Qunye Zhang, Shandong (CN); Weijian Wang, Shandong (CN); Hongming Du, Liaoning (CN); Congcong Wang, Shandong (CN); Baojian Hang, Shandong (CN); Fengshan Wang, Shandong (CN)

(73) Assignees: Shandong University, Shandong (CN); Shandong Institute for Food and Drug Control, Shandong (CN); Avanc Pharmaceutical Co., Ltd, Liaoning (CN)

( * ) Notice: Subject to any disclaimer, the term of this patent is extended or adjusted under 35 U.S.C. 154(b) by 0 days.

(21) Appl. No.: 17/389,382

(22) Filed: Jul. 30, 2021

(65) Prior Publication Data
US 2022/0034853 A1    Feb. 3, 2022

(30) Foreign Application Priority Data
Jul. 30, 2020    (CN) .................. 202010754240.6

(51) Int. Cl.
| | |
|---|---|
| *C07K 5/00* | (2006.01) |
| *G01N 30/72* | (2006.01) |
| *C12N 9/74* | (2006.01) |
| *C12Q 1/37* | (2006.01) |
| *G01N 30/06* | (2006.01) |

(52) U.S. Cl.
CPC ............. *C12N 9/6429* (2013.01); *C12Q 1/37* (2013.01); *G01N 30/06* (2013.01); *G01N 30/7206* (2013.01)

(58) Field of Classification Search
None
See application file for complete search history.

*Primary Examiner* — Celine X Qian
(74) *Attorney, Agent, or Firm* — JCIP Global Inc.

(57) ABSTRACT

The present invention provides a snake venom thrombin marker peptide of *Agkistrodon Halys Pallas* and an application of the snake venom thrombin-like enzyme in identifying species of Hemocoagulase for Injection. The application includes the following steps of: dissolving a to-be-detected sample and a reference substance of the marker peptide respectively to prepare a test solution and a reference solution, and conducting alkylation reduction on the test solution and the reference solution with dithiothreitol and iodoacetamide; after diluting products with an ammonium bicarbonate solution, adding enzyme for hydrolysis; and after enzymolysis is finished, conducting centrifugation at a high speed, and injecting a supernatan into a liquid chromatography-mass spectrometer for analysis. This method is simple, convenient and rapid, is strong in specificity, fills the gap in identifying the source of species of the snake venom thrombin-like enzyme of *Agkistrodon Halys Pallas* and improves the quality control level.

Figure 1:
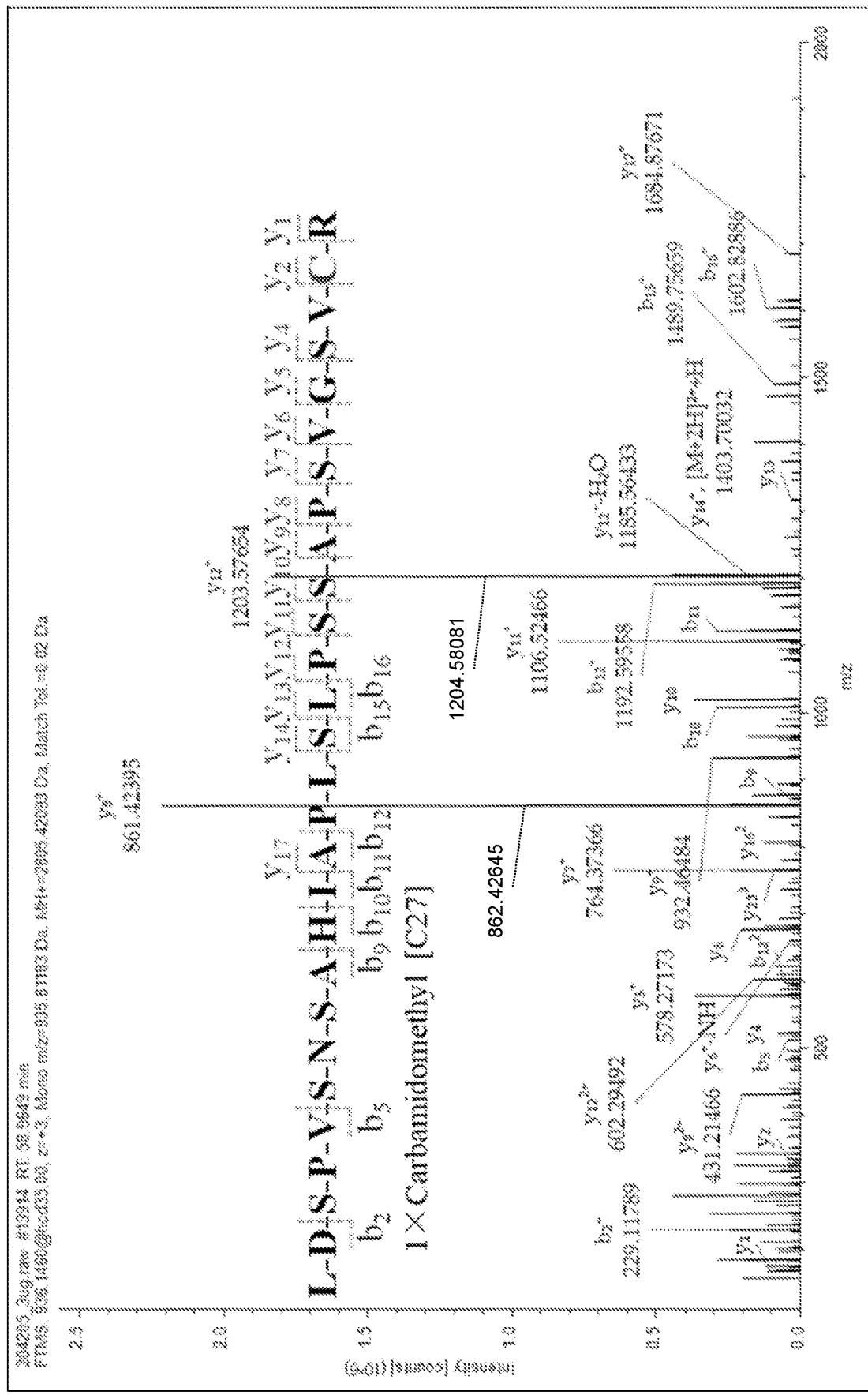

3 Claims, 6 Drawing Sheets
Specification includes a Sequence Listing.

SEQUENCE LISTING

<160> NUMBER OF SEQ ID NOS: 1

<210> SEQ ID NO 1
<211> LENGTH: 28
<212> TYPE: PRT
<213> ORGANISM: Gloydius ussuriensis

<400> SEQUENCE: 1

Leu Asp Ser Pro Val Ser Asn Ser Ala His Ile Ala Pro Leu Ser Leu
1               5                   10                  15

Pro Ser Ser Ala Pro Ser Val Gly Ser Val Cys Arg
            20                  25

SNAKE VENOM THROMBIN-LIKE ENZYME MARKER PEPTIDE OF *AGKISTRODON HALYS PALLAS* AND ITS APPLICATION IN THE SPECIES IDENTIFICATION OF HEMOCOAGULASE FOR INJECTION

CROSS-REFERENCE TO RELATED APPLICATION

This application claims the priority benefit of China application serial no. 202010754240.6, filed on Jul. 30, 2020. The entirety of the above-mentioned patent application is hereby incorporated by reference herein and made a part of this specification.

BACKGROUND

Technical Field

The present invention relates to a snake venom thrombin marker peptide of *Agkistrodon Halys Pallas* and an application of the snake venom thrombin marker peptide in identifying species of snake venom thrombin for injection and belongs to the field of identifying the species of snake venom thrombin products.

Description of Related Art

Snake venom thrombin drugs are hemostatics originated from different snake species. The main active ingredient is snake venom thrombin which is a type of serine protease having the arginine esterase activity and the amido enzyme activity, may play a key role in coagulation and is mainly used in treatment of hemorrhagic diseases. Currently, the snake venom thrombin drugs approved for market in China mainly include Hemocoagulase for Injection (Bangting®), Hemocoagulase *Bothrops Atrox* for Injection (Baquting®), Haemocoagulase *Agkistrodon* for Injection (Suling®) and the snake venom thrombin injection produced by Zhaoke Pharmaceutical (Hefei) Co., Ltd. (Slounase®).

The current quality standard of the snake venom thrombin drugs is mainly identified by biochemical reaction, chemical chromogenic reaction, liquid chromatography-peptide graph control method, gel electrophoresis method or the like, but these methods cannot identify the source of species of the biochemical drugs or define the source of species of the unknown samples. Since the snake venom thrombin originated from different snake species is different in structure, differences can be found in the mechanism of action and corresponding pharmacological action, so that it is necessary to establish an identification and detection method for the snake venom thrombin drugs with the specific specificity for strengthening the quality control of such products and ensuring the safety of clinical drugs.

SUMMARY

In order to solve the above technical problems, the present invention provides a snake venom thrombin-like enzyme of *Agkistrodon Halys Pallas* and an application of the snake venom thrombin-like enzyme in identifying species of Hemocoagulase for Injection. The method of identifying the species of marker peptide provided by the present invention is simple, convenient and rapid, is strong in specificity, fills the gap in the quality standard of Hemocoagulase for Injection, improves the quality control level and is beneficial to ensuring the safety and the effectiveness of clinical medication.

To achieve the above inventive objective, the present invention employs the following technical solution:

Provided is a snake venom thrombin-like enzyme of *Agkistrodon Halys Pallas*, an amino acid sequence of which is: LDSPVSNSAHIAPLSLPSSAPSVGSVCR (SEQ ID NO. 1).

Provided is an application of the snake venom thrombin-like enzyme of *Agkistrodon Halys Pallas* in identifying species of Hemocoagulase for Injection.

Preferably, an application method of snake venom thrombin-like enzyme of *Agkistrodon Halys Pallas* in identifying the species of Hemocoagulase for Injection includes the following steps of:

A: dissolving the Hemocoagulase for Injection and the snake venom thrombin-like enzyme of *Agkistrodon Halys Pallas* into a test solution and a reference solution respectively;

B: conducting alkylation reduction treatment on the test solution and the reference solution with dithiothreitol and iodoacetamide;

C: after alkylation reduction is finished, diluting products with an ammonium bicarbonate solution, and adding enzyme liquid for hydrolysis;

D: after enzymolysis is finished, conducting centrifugation at a high speed, and injecting a supernatant into a liquid chromatography-mass spectrometer for analysis; and E: when detecting an ion flow chromatography extracted from the ion pairs, if the test solution has a chromatographic peak with a retention time consistent with that of the reference solution, indicating that a to-be-detected sample contains an amino acid sequence of SEQ ID NO. 1, and proving that the to-be-detected sample is originated from *Agkistrodon Halys Pallas*, or otherwise the to-be-detected sample is not originated from *Agkistrodon Halys Pallas*.

Preferably, the ion pairs for detection in the step E are tricharged 935.8→861.4 and tricharged 935.8→602.3.

Preferably, the application method of the snake venom thrombin marker peptide of *Agkistrodon Halys Pallas* in identifying the species of the snake venom thrombin for injection specifically includes the following steps of:

(1) putting 10 mg of the snake venom thrombin-like enzyme of *Agkistrodon Halys Pallas* "LDSPVSNSA-HIAPLSLPSSAPSVGSVCR" in a 10 mL measuring flask, dissolving the snake venom thrombin-like enzyme with water to a constant volume, conducing uniform mixing to prepare 1 mg/ml reference stock solution 1, dissolving 10 µL of the reference stock solution 1 with the water to a constant volume of 10 ml to prepare 1 µg/ml reference stock solution 2, dissolving 600 µL of the reference stock solution 2 with a 25 mmol/L ammonium bicarbonate solution to a constant volume of 10 mL to prepare a 60 ng/mL reference solution, and dissolving 50 mg of a to-be-detected sample with 500 µL of a 25 mmol/L ammonium bicarbonate solution to obtain the test solution;

(2) weighing 400 µL of the test solution and the reference solution respectively, adding 20 µL of a 0.4 mol/L dithiothreitol solution for uniform mixing, conducting reaction for 1 h at 60° C., and adding 40 µL of a 0.4 mol/L iodoacetamide solution, placing a product in the dark for 30 min, adding 10 µL of 0.4 µg/µL trypsin for enzymolysis for 1 h at 37° C., conducting inactivation for 10 min at 90° C., taking the product out for cooling to a room temperature, conducting centrifugation for 10 min at 1200 rpm, and injecting a supernatant into a liquid chromatography-mass spectrometer for analysis; and (3) when detecting an ion flow chromatography extracted from the ion pairs, if the test solution has a chromatographic peak with a retention time consistent with that of the reference solution, indicating that a to-be-detected sample contains an amino acid sequence of SEQ ID NO. 1, and proving that the to-be-detected sample is originated from the *Agkistrodon Halys Pallas*, or otherwise the to-be-detected sample is not originated from *Agkistrodon Halys Pallas.*

Preferably, the liquid phase and mass spectrum test conditions of the liquid chromatography-mass spectrometer are as follows:

chromatography-mass spectrometry conditions: a chromatographic column is a Waters ACQUITY UPLC™ BEH $C_{18}$ chromatographic column (50 mm×2.1 mm, 1.7 μm); a mobile phase A is 0.1% formic acid solution, and a mobile phase B is 0.1% formic acid acetonitrile; a column temperature is 40° C.; the sample size is 2 μL; the flow rate is 0.2 mL/min; and an elution program is as follows: 0→1 min, mobile phase A: 80%; 1→5 min, mobile phase A 80%→10%; 5→7 min, mobile phase A 10%→10%.

Mass spectrum conditions: ESI source, positive ion scanning mode, multi-reaction monitoring; vortex ion spraying temperature: 500° C.; ionization potential: 5.5 kV; outlet potential of the collision chamber: 10 V; inlet potential: 10 V; tricharged 935.8→861.4 and tricharged 935.8→602.3 as ion pairs for test, and the collision potential is respectively: 45 V and 40 V, declustering potential: 135V.

The present invention has the following beneficial effects that:

(1) The present invention conducts library searching and comparison after integrating a protein library and a venom protein library of current snack species by using NCBI and UniProt and finds out marker peptide LDSPVSNSA-HIAPLSLPSSAPSVGSVCR (SEQ ID NO. 1) of the snake venom thrombin-like enzyme (SVTLE) from *Agkistrodon Halys Pallas* by combining with large experimental researches. Since it has been known that amino acid sequences of SVTLE from other snake species, including *Bothrops atrox, Vipera russelli siamensis* and *Deinagkistrodon acutus* do not contain this fragment of amino acid sequence, the marker peptide may be used for specifically characterizing thrombin-like enzyme in the venom of *Agkistrodon Halys Pallas.*

(2) The traditional method of identifying thrombin-like enzyme cannot identify the species, but the method of identifying the species of the marker peptide provided by the present invention is simple, convenient and rapid, is strong in specificity, fills the gap in the quality standard of *Agkistrodon Halys Pallas* Hemocoagulase for Injection, improves the quality control level of such drug greatly and is beneficial to ensuring the safety and the effectiveness of clinical medication.

BRIEF DESCRIPTION OF THE DRAWINGS

FIG. 1 shows tandem mass spectrogram spectra of a marker peptide of SVTLE from *Agkistrodon Halys Pallas* and fragment assignment.

FIG. 2 shows mass spectrogram spectra of the marker peptide of the SVTLE from *Agkistrodon Halys Pallas.*

FIG. 3 shows an ion chromatography extracted from a blank solution.

FIG. 4 shows an ion chromatography extracted from a marker peptide of a reference solution.

FIG. 5 shows an ion chromatography extracted from Hemocoagulase for Injection.

FIG. 6 shows an ion chromatography extracted from the Hemocoagulase *Bothrops Atrox* for Injection.

DESCRIPTION OF THE EMBODIMENTS

The present invention will be further described below in combination with specific embodiments:

Preparation methods for relevant reagents and solutions in the following embodiments are as shown below:

(1) Reagent: trypsin (Sigma, Batch No.: SLBS8956), SVTLE of *Agkistrodon halys* (Avanc Pharmaceutical Co., Ltd., Purity: 98.5%), guanidine hydrochloride (VETEC, Batch No.: WXBC4261V), tromethamine (Shanghai, Batch No.: 20181206), dithiothreitol (BBI Life Sciences, Batch No.: D911BA0011), iodoacetamide (BBI Life Sciences, Batch No.: B326BA1943), while other reagents are all analytically pure.

(2) 25 mmol/L ammonium bicarbonate solution: weighing 79.06 mg of ammonium bicarbonate, and then dissolving the ammonium bicarbonate with 40 mL of water to obtain the solution.

(3) 0.4 mol/L dithiothreitol (DTT) solution: weighing 15.42 mg of dithiothreitol, and then dissolving the dithiothreitol with 250 μL of water to obtain the solution.

(4) 0.4 mol/L Iodoacetamide (IA) solution (which is newly prepared upon use): weighing 18.5 mg of iodoacetamide, and then dissolving the iodoacetamide with 250 μL of water to obtain the solution.

(5) 0.4 mg/mL trypsin solution (which is newly prepared upon use): weighing 8.0 mg of trypsin, and then dissolving the trypsin with 20 mL of water to obtain the solution.

Embodiment 1 Screening and confirmation of marker peptide.

1. Instrument and Equipment

Thermo Fusion high resolution mass spectrometer (Thermo Fisher Scientific, America), EASY-nLC 1000 nL Nanoscale liquid chromatograph (Thermo Fisher Scientific, America), CP225D electronic scales (Sartorius, Germany), Sigma 3-30 K refrigerated centrifuge (Sigma, Germany), Millipore Milli-QAdvantage A10 Ultra-Pure Water Purifier (Millipore, America).

2. Conditions for LC-MS/MS

Chromatographic column: desalting and enrichment were conducted by using a 0.2 mm×3.5 cm (5 μm particle size) ReproSil®-Pur C18-AQ Trap column made in the laboratory, and 75 μm×25 cm (3 μm particle size) ReproSil®-Pur C18-AQ nanoliter analytical column made in the laboratory was employed for separation. A mobile phase A is a 0.1% formic acid solution of 2% acetonitrile, while a mobile phase B is a 0.1% formic acid solution of 98% acetonitrile. The flow rate of nanoliter separation pump is 300 nL/min, and gradient elution settings are as shown in Table 1 below.

TABLE 1

Table Gradient Elution for Nanoliter Liquid Phase-High Resolution Mass Spectrum

| Time (min) | Mobile Phase A (nL/min) | Mobile Phase B (nL/min) |
|---|---|---|
| 0 | 300 | 0 |
| 3 | 300 | 0 |
| 5 | 300 | 0 |
| 20 | 270 | 30 |
| 75 | 204 | 96 |
| 95 | 150 | 150 |

TABLE 1-continued

Table Gradient Elution for Nanoliter Liquid
Phase-High Resolution Mass Spectrum

| Time (min) | Mobile Phase A (nL/min) | Mobile Phase B (nL/min) |
|---|---|---|
| 100 | 0 | 300 |
| 100.5 | 0 | 450 |
| 108 | 0 | 450 |
| 110 | 450 | 0 |
| 115 | 450 | 0 |
| 120 | 450 | 0 |

Mass spectrum conditions: positive ion mode was employed for analysis, wherein the spray voltage was 2.0 kV, a temperature of an ion transport capillary was 275° C., and the transmission efficiency of S-Lens was set as 60%. Orbitrap (an ion trap mass analyzer) was taken as a mass analyzer for a primary mass spectrum, wherein a resolution ratio was 60,000, and a collection scope was 350-1650. IT was taken as a mass analyzer for a secondary mass spectrum, a Rapid Scan mode was employed for scanning, and an HCD mode was employed for fracturing, and the fracturing energy NCE was set as 35%.

3. Data Collection 5 mg of SVTLE from *Agkistrodon Halys Pallas* was put in a 10 mL measuring flask and was dissolved with 25 mmol/L ammonium bicarbonate solution to a constant volume; 200 μL of the solution was precisely measured, 10 μL of a 0.2 mol/L dithiothreitol solution was added, a mixture was blended uniformly and reacted for 1 h at 60° C., 20 μL of a 0.2 mol/L iodoacetamide solution was added, a mixture was placed in the dark for 30 min, 760 μL of the 25 mmol/L ammonium bicarbonate solution and 10 μL of a 0.4 mg/mL trypsin solution (which was newly prepared upon use) were added, the mixture was reacted for 90 min at 37° C. and inactivated for 10 min at 90° C.; a product was desalted and dried up with a $C_{18}$ solid-phase extraction column, redissolving was conducted with 200 μL of water, centrifugation was conducted for 10 min at 1200 rpm, and a supernatant was taken as a test solution that is injected via nanoliter liquid separation, and the primary mass spectrum and the secondary mass spectrum were collected by using a high resolution mass spectrum.

4. Screening and Confirmation with Library Searching

Figure 2:
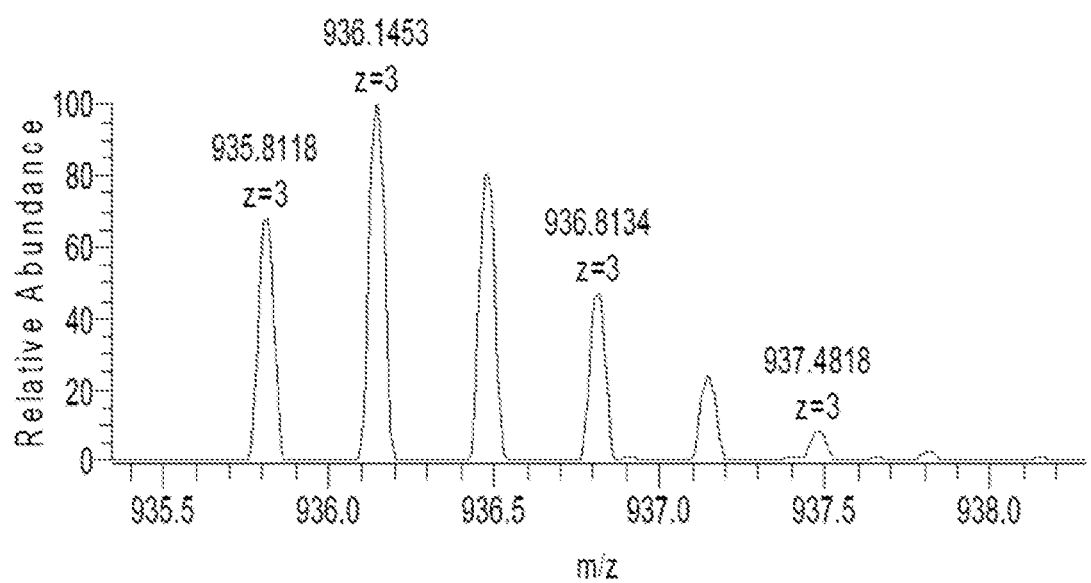

NCBI and UniProt were applied to integrate the relevant snack protein library and venom protein library, and then a snack and venom database was established. Based on a Peptidemass function provided by the UniProt, results of enzymatically hydrolysing SVTLE proteins of different species with trypsin was simulated, and a sequence of the marker polypeptide of *Agkistrodon Halys Pallas* relative to other species was obtained by comparing a protein sequence of thrombin-like enzyme from *Agkistrodon Halys Pallas* with that in other species, and a mass spectrum database was searched by using Proteome Discoverer Software (Version 2.2) and "LDSPVSNSAHIAPLSLPSSAPSVGSVCR" was confirmed as the marker peptide of the SVTLE from *Agkistrodon Halys Pallas* by referring to the principles of (1) 8-25 amino acids; (2) voiding artificially modified easily as much as possible; and (3) no omission of restriction site in digestion, etc. According to the detection result, the molecular weight and the secondary mass spectrum of marker peptide are in consistence with theoretical values as shown in FIG. 1 and FIG. 2.

Embodiment 2

1. Instrument and Equipment

SCIEX Triple Quad 6500 Mass Spectrometer, CP225D Electronic Scales (Sartorius, Germany), Sigma 3-30 K Refrigerated Centrifuger (Sigma, Germany), Milli-QAdvantage A10 UP Water Purification System (Millipore, America).

2. Chromatograph-Mass Spectrum Conditions

Liquid phase conditions: the chromatographic column is Waters ACQUITY UPLC™ BEH $C_{18}$ chromatographic column (50 mm×2.1 mm, 1.7 μm); and a mobile phase A is 0.1% formic acid solution and a mobile phase B is 0.1% formic acid acetonitrile for gradient elution, wherein the elution program is as follows: 0→1 min, mobile phase A: 80%; 1→5 min, mobile phase A 80%→10%; 5→7 min, mobile phase A 10%→10%; column temperature: 40° C.; sample size: 2 μL; flow rate: 0.2 mL/min;

Mass spectrum conditions: ESI source, positive ion scanning mode, multi-reaction monitoring; vortex ion spraying temperature: 500° C.; ionization potential: 5.5 kV; outlet potential of the collision chamber: 10 V; inlet potential: 10 V; tricharged 935.8→861.4 and tricharged 935.8→602.3 was taken as ion pairs for detection with collision potential of 45 V and 40 V respectively and declustering potential of 135V.

3. Solution Preparation (1) Reference solution: 10 mg of a reference substance of the snake venom thrombin-like enzyme of *Agkistrodon Halys Pallas* (with an amino acid sequence of "LDSPVSNSAHIAPLSLPSSAPSVGSVCR") prepared in Embodiment 1 in a 10 mL measuring flask and was dissolved with water to a constant volume, uniform mixing was conducted to prepare a reference stock solution 1 with a concentration of 1 mg/ml; 10 μL of the reference stock solution 1 was dissolved with water to a constant volume of 10 ml to prepare a reference stock solution 2 with a concentration of 1 μg/ml; 600 μL of the reference stock solution 2 was dissolved with a 25 mmol/L ammonium bicarbonate solution to a constant volume of 10 mL to prepare a 60 ng/mL reference solution;

(2) Test solution: 50 mg of a to-be-detected sample was dissolved with 500 μL of a 25 mmol/L ammonium bicarbonate solution to obtain the test solution; and (3) Blank solution: the 25 mmol/L ammonium bicarbonate solution was taken as the blank solution of the reagent;

4. Enzymolysis Treatment

400 μL of the test solution, 400 μL of the reference solution and 400 μL of the blank solution were precisely weighed, 20 μL of 0.4 mol/L dithiothreitol solution was added for uniform mixing, and reaction was conducted for 1 h at 60° C.; 40 μL of a 0.4 mol/L iodoacetamide solution was added, a product was placed in the dark for 30 min, and 10 μL of 0.4 μg/μL trypsin was added for reaction for 1 h at 37° C.; and inactivation was conducted for 10 min at 90° C., a product was taken out for cooling to a room temperature, centrifugation was conducted for 10 min at 1200 rpm, and a supernatant was injected into a liquid chromatography-mass spectrometer for analysis.

5. Specificity

Figure 3:
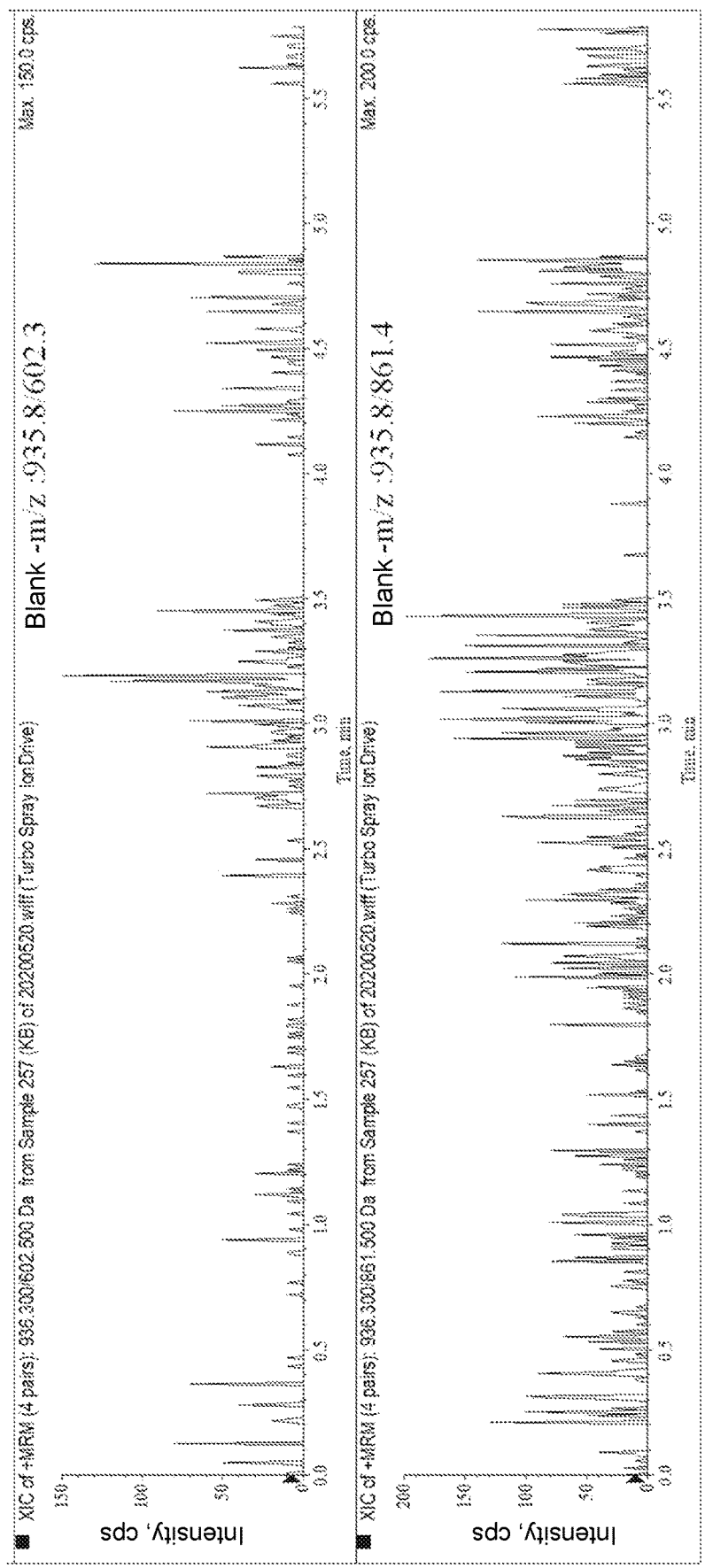
Figure 4:
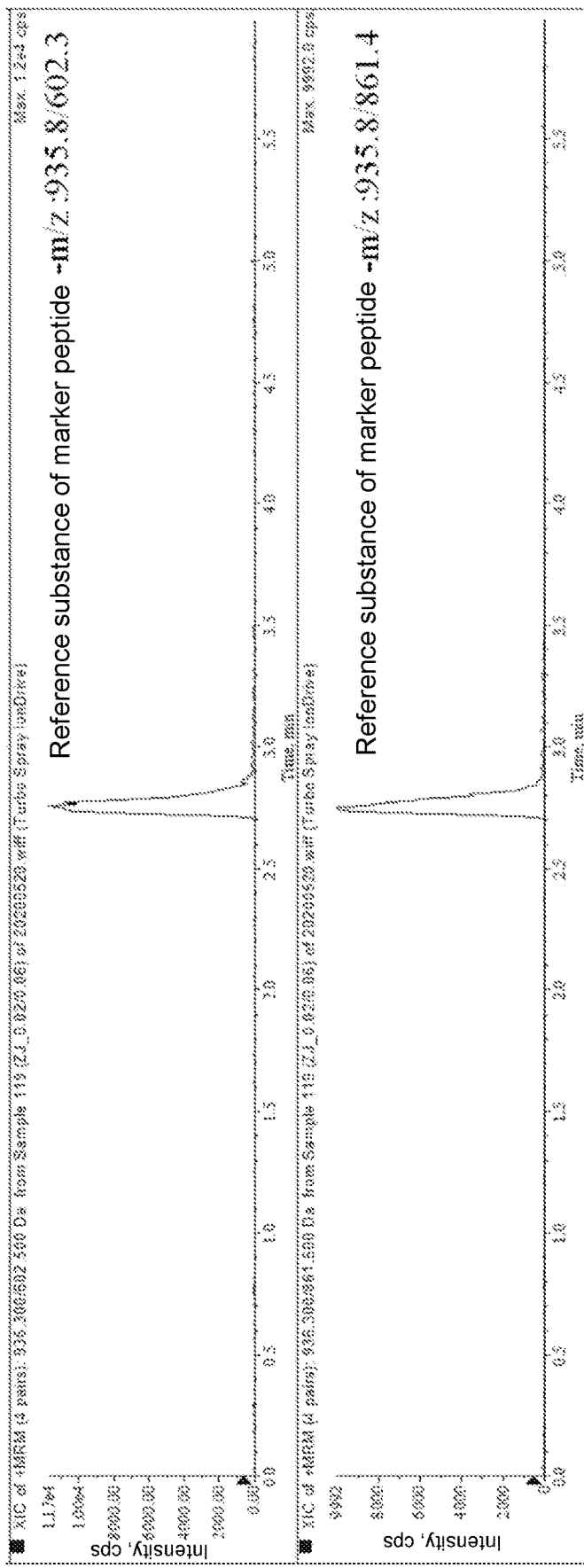
Figure 5:
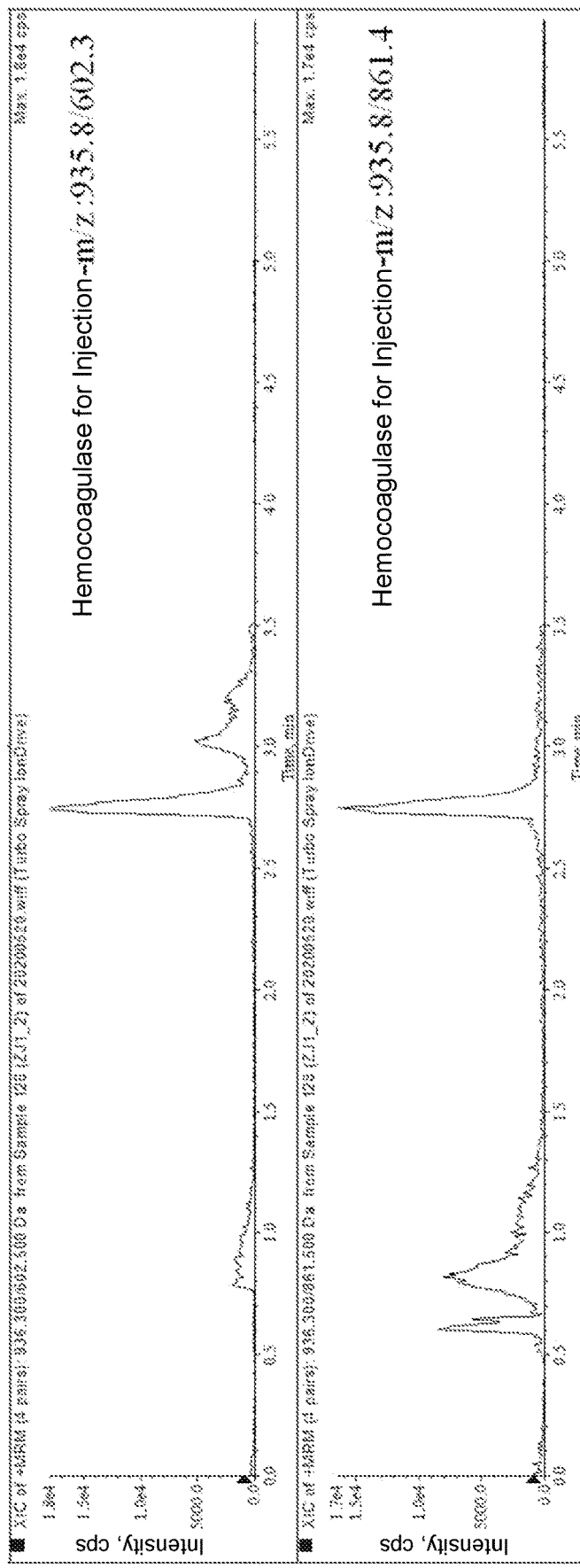
Figure 6:
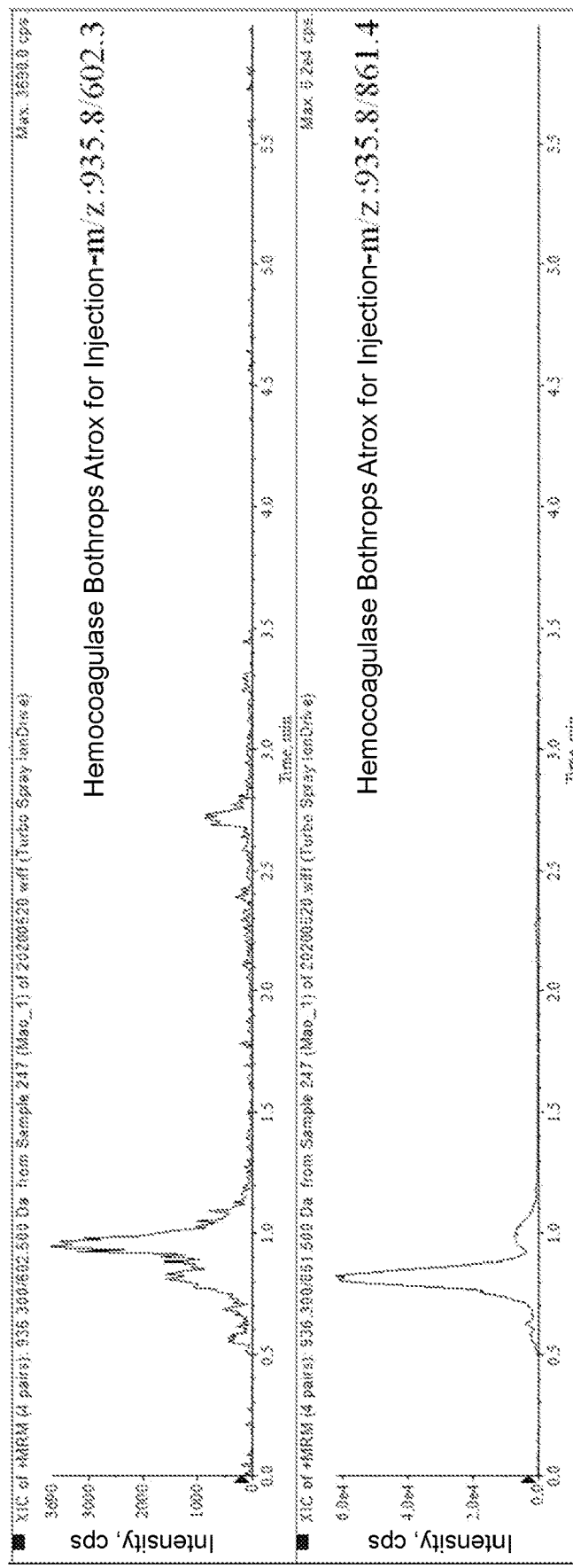

2 μL of the test solution, 2 μL of the blank solution and 2 μL of the reference were taken for liquid quality analysis according to the liquid mass spectrum conditions in Item 2, and results showed that, the blank solution had no interference peak at the position that a peak appeared of the reference solution, while the test solution had a responded chromatographic peak at the position that a peak appeared of the reference solution, indicating that the method was good in specificity, as shown in FIGS. 3-5.

6. Limit of Detection and Limit of Quantification

The reference solutions were treated with enzymolysis and were diluted to concentrations of 3 ng/mL and 9 ng/mL respectively for sample injection with the quantity of 2 μL and detection was conducted with tricharged 935.8→861.4 of the marker peptide as the quantitative ions, wherein the signal-to-noise ratios were respectively 3.1 and 9.8. Thus, the limit of detection and the limit of quantification were 3 ng/mL and 9 ng/mL respectively.

7. Precision

The test solution was taken for continuous and repeated sample injection for 6 times, a tricharged 935.8→861.4 ion pair chromatogram was extracted, and showing that a peak area RSD of sample injection for 6 times was 1.9%), and the precision of an instrument was good.

8. Stability

The test solution was placed at 8° C. after being treated, and determined with sample injection after 0 h, 2 h, 4 h, 6 h, 8 h, 16 h and 24 h respectively, a tricharged 935.8→861.4 ion pair chromatogram was extracted, and a peak area RSD was 2.5%, indicating that the solution to be detected was stable within 24 h at 8° C.

TABLE 2

| Time (h) | Peak Area | Mean Value | RSD |
|---|---|---|---|
| 0 | 6.90E+04 | 7.12E+04 | 2.5% |
| 2 | 6.95E+04 | | |
| 4 | 7.25E+04 | | |
| 8 | 7.05E+04 | | |
| 16 | 7.34E+04 | | |
| 24 | 7.21E+04 | | |

9. Durability

The test solution and the reference solution were taken with keeping other conditions invariant and changing the elution program only, as follows: 0→3 min, mobile phase A 95%; 3→8 min, mobile phase A 95%→10%; 8.1→40 min, mobile phase A 10%→10%. If after the elution program was changed, the test solution still had a corresponding chromatographic peak at the position that a peak appeared of the reference solution, it was showed that the method was free of the impact of the elution program and was good in durability.

TABLE 3

| Sample Name | Retention Time (min) | 935.8→861.4 | 935.8→602.3 |
|---|---|---|---|
| Reference substance of marker peptide | 5.15 | 5.19E+04 | 4.45E+04 |
| Test solution | 5.15 | 6.82E+04 | 5.85E+04 |

The test solution and the reference solution were taken with keeping other conditions invariant and replacing a chromatographic column with Thermo Accucore ™ $C_{18}$ chromatographic column (50 mm×2.1 mm, 2.6 μm) only. If after the elution program was changed, the test solution still had a corresponding chromatographic peak at the position that a peak appeared of the reference solution, it was showed that the method was free of the impact of the chromatographic column brand and was good in durability.

TABLE 4

| Sample Name | Retention Time (min) | 935.8→861.4 | 935.8→602.3 |
|---|---|---|---|
| Reference substance of marker peptide | 2.45 | 4.93E+04 | 4.25E+04 |
| Test solution | 2.45 | 6.43E+04 | 5.74E+04 |

10. Experimental Result

Samples of Hemocoagulase for Injection (Bangting®), Hemocoagulase *Bothrops Atrox* for Injection (Baquting®), Hemocoagulase *Agkistrodon* for Injection (Suling®) and Hemocoagulase for Injection (Slounase®) (unmarked with the snake species) respectively according to the method specified in Item 3, detection was conduction according to the method specified in Item 2, and results are as shown in Table 5.

According to the pretreatment method and analysis method for a venom sample mentioned above, detection results show that, by mass-to-charge ratio (m/z), with 935.8→861.4 and 935.8→602.3 as the detection ion pairs, in the extracted ion flow chromatography of the test solution, three batches of Hemocoagulase for Injection (Bangting®) have chromatographic peak with a chromatographic retention time consistent with that (2.75 min) of the reference substance of the marker peptide, while no chromatographic peak is extracted in three batches of Hemocoagulase *Bothrops Atrox* for Injection (Baquting®), one batch of Hemocoagulase *Agkistrodon* for Injection (Suling®) and one batch of Hemocoagulase Injection (Slounase®) at the chromatographic retention time of the reference substance of the marker peptide. Thus, the marker peptide LDSPVSNSA-HIAPLSLPSSAPSVGSVCR (SEQ ID NO. 1) may be detected in all the three batches of samples marked as Hemocoagulase for Injection (Bangting®), and the source is confirmed as *Agkistrodon Halys Pallas*. Since such marker peptide is not detected in three batches of Hemocoagulase *Bothrops Atrox* for Injection (Baquting®), one batch of Hemocoagulase *Agkistrodon* for Injection (Suling®) and one batch of Hemocoagulase Injection (Slounase®), it can be confirmed that these 5 batches of venoms are not originated from the *Agkistrodon Halys Pallas*.

TABLE 5

| Test Result of To-be-detected Samples | | | | |
|---|---|---|---|---|
| Name of Variety | Batch No. | 935.8→861.4 Retention Time (min) | 935.8→602.3 Retention Time (min) | Originated from Agkistrodon Halys or Not |
| Reference substance of marker peptide | / | 2.75 | 2.75 | / |
| Hemocoagulase for Injection (Bangting) | 20200311 | 2.75 | 2.75 | Yes |

TABLE 5-continued

Test Result of To-be-detected Samples

| Name of Variety | Batch No. | 935.8→861.4 Retention Time (min) | 935.8→602.3 Retention Time (min) | Originated from Agkistrodon Halys or Not |
|---|---|---|---|---|
| Hemocoagulase for Injection (Bangting) | 20200312 | 2.74 | 2.74 | Yes |
| Hemocoagulase for Injection (Bangting) | 20200313 | 2.75 | 2.75 | Yes |
| Hemocoagulase Bothrops Atrox for Injection (Baquting) | 1806263 | 0.85 | 0.98 | No |
| Hemocoagulase Bothrops Atrox for Injection (Baquting) | 1901072 | 0.85 | 0.96 | No |
| Hemocoagulase Bothrops Atrox for Injection (Baquting) | 1901073 | 0.84 | 0.98 | No |
| Hemocoagulase Agkistrodon for Injection (Suling) | 22001072 | / | 0.60 | No |
| Hemocoagulase Injection (Slounase) | 20191107 | / | / | No |

What is claimed is:

1. An method of using a snake venom thrombin marker peptide of *Agkistrodon Halys Pallas* in identifying species of snake venom thrombin for injection, wherein the snake venom thrombin marker peptide of *Agkistrodon Halys Pallas* comprises the amino acid sequence of SEQ ID NO. 1 and the method comprises the following steps of: A: dissolving the snake venom thrombin for injection and the snake venom thrombin marker peptide of *Azkistrodon Halys Pallas* into a test solution and a reference solution respectively; B: conducting an alkylation reduction treatment on the test solution and the reference solution with dithiothreitol and iodoacetamide; C: after the alkylation reduction treatment is finished, adding enzyme for a hydrolysis; D: after the hydrolysis is finished, conducting centrifugation at a high speed, and injecting a supernatant into a liquid chromatography-mass spectrometer for analysis; and E: when detecting an ion flow chromatography extracted from ion pairs, if the test solution has a chromatographic peak with a retention time in consistence with the reference solution, indicating that a to-be-detected sample contains the amino acid sequence of SEQ ID NO. 1, and proving that the to-be-detected sample is originated from *Agkistrodon Halys Pallas*, or otherwise the to-be-detected sample is not originated from *Agkistrodon Halys Pallas*.

2. The method according to claim 1, wherein liquid phase and mass spectrum test conditions of the liquid chromatography-mass spectrometer mentioned in the step E are as follows:

chromatography-mass spectrometry conditions: a $C_{18}$ chromatographic column having 50 mm length+ and 2.1 mm inner diameter and containing, 1.7 μm particle size; a mobile phase A is 0.1% formic acid solution, and a mobile phase B is 0.1% formic acid acetonitrile; a column temperature is 40° C.; the sample size is 2 μL; a flow rate is 0.2 mL/min; and an elution program is as follows: 0→1 min, the mobile phase A: 80%; 1→5 min, the mobile phase A 80%→10%; and 5→7 min, mobile phase A 10%→10%; and mass spectrometry conditions: electrospray ionization (ESI) source, positive ion scanning mode, multi-reaction monitoring; vortex ion spraying temperature: 500° C.; ionization potential: 5.5 kV; outlet potential of a collision chamber: 10 V; inlet potential: 10 V; with tricharged 935.8→861.4 and tricharged 935.8→602.3 as ion pairs for detection, collision potential: 45 V and 40 V respectively, declustering potential: 135V.

3. The method according to claim 1, wherein the step A comprising the following specifically steps: putting 10 mg of the snake venom thrombin marker peptide of *Agkistrodon Halys Pallas* in a 10 mL measuring flask, dissolving the snake venom thrombin marker peptide with water to a constant volume, conducting uniform mixing to prepare a 1 mg/ml reference stock solution 1, dissolving 10 μL of the reference stock solution 1 with the water to a constant volume of 10 ml to prepare a 1 μg/ml reference stock solution 2, dissolving 600 μL of the reference stock solution 2 with a 25 mmol/L ammonium bicarbonate solution to a constant volume of 10 mL to prepare a 60 ng/mL reference solution, and dissolving 50 mg of a to-be-detected sample with 500 μL of a 25 mmol/L ammonium bicarbonate solution to obtain a test solution; and wherein the steps B, C and D comprising the following specifically steps: weighing 400 μL of the test solution and the reference solution respectively, adding 20 μL of a 0.4 mol/L dithiothreitol solution for uniform mixing, conducting reaction for 1 h at 60° C., adding 40 μL of a 0.4 mol/L iodoacetamide solution to obtain a product, placing the product in dark for 30 min, adding 10 μL of 0.4 μg/μL trypsin for enzymolysis for 1 h at 37° C., conducting inactivation for 10 min at 90° C., taking the inactivated product out for cooling to a room temperature, conducting centrifugation for 10 min at 1200 rpm, and injecting a supernatant into a liquid chromatography-mass spectrometer for analysis.

* * * * *